US00PP08674P

United States Patent [19]

Goffreda

[11] Patent Number: Plant 8,674

[45] Date of Patent: Apr. 5, 1994

[54] APRICOT TREE NJA54

[75] Inventor: Joseph C. Goffreda, Kendall Park, N.J.

[73] Assignee: Rutgers University, New Brunswick, N.J.

[21] Appl. No.: 978,430

[22] Filed: Nov. 18, 1992

[51] Int. Cl.[5] ..... A01H 5/00

[52] U.S. Cl. ..... Plt./39

[58] Field of Search ..... Plt. 39

*Primary Examiner*—James R. Feyrer
*Assistant Examiner*—Elizabeth C. Kemmerer
*Attorney, Agent, or Firm*—Frank B. Robb

[57] ABSTRACT

A new apricot tree cultivar producing early maturing fruit of very good dessert and canning qualities.

1 Drawing Sheet

BACKGROUND OF THE DISCLOSURE

This invention relates to a new and distinct cultivar of apricot tree, developed near Cream Ridge, N.J., as part of an extensive program to develop improved apricot trees having early maturing fruit of excellent dessert and canning quality.

The cultivar of this inventiton is a seedling whose parentage is known, and was selected from a block planted near Cream Ridge, N.J., in a cultivated area of other trees whose breeding records are also kept.

The new cultivar which I have chosen to designate as NJA54, was produced by crossing a seedling known as NJA2, being the seed parent, and another selection, RR17-62, being the pollen parent.

I have found during continued growth of the trees of this cultivar, that it produces a vigorous, upright tree with fruit of excellent dessert and canning quality.

The tree flowers at about the same time as the cultivar known as "Harcot" (unpatented), and the apricot fruit produced has excellent quality with a firm texture.

During the course of the several years of observing the growth it is noted that I have caused the selection to be asexually propagated by grafting on peach rootstocks at Cream Ridge, N.J.

The selected tree was of grafted material which has maintained the desired characteristics after propagation in successive generations.

Figure 1:
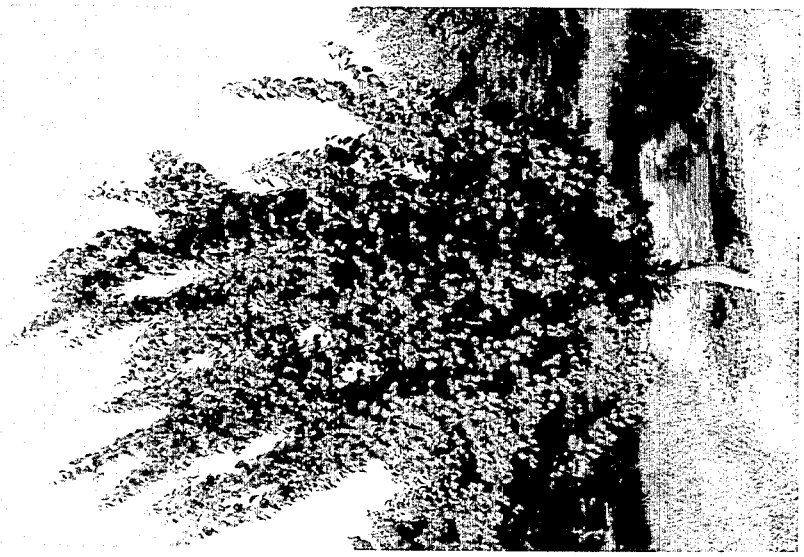

In support of the disclosure herein, the drawing included, in FIG. 1, shows a typical example of a young tree of the new cultivar illustrating the growth habit.

Figure 2:
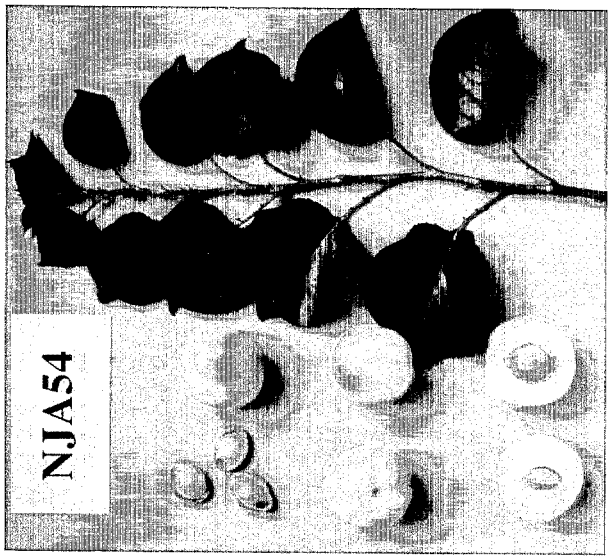

FIG. 2 shows a typical example of the apricot produced, disclosing the color, globose, slightly compressed shape, fresh color, and blush with the skin color, as well as typical examples of the seeds and leaves, disclosing their color and shape.

In describing the tree and fruit in particular detail, reference is had to the Horticultural Color Chart issued by the British Color Council in collaborattion with The Royal Horticultural Society. Color was also measured in terms of its color space coordinates (L*a*b) with a Minolta CR-300 Croma Meter calibrated with a white calibration plate. The photographs forming the drawing herein are as nearly like the actual fruit and tree as it is possible to make the same in a color reproduction of this kind.

Turning to the details of this new cultivar, we note that the following is a detailed description embodying the primary distinctive characteristics and identifying means by which the tree is recognized and the fruit produced is described.

FRUIT

Shape: Globose, slightly compressed.

Average size: Axial diameter 4.1 cm (1.6 inches); transverse diameter in suture plane 4.2 cm (1.65 inches); transverse diameter at right angles to suture plane 3.9 cm (1.5 inches).

Average mass: 42 g

Skin color: Undercolor is orpiment orange to nasturium orange Plates 25a to 25b (L=59.47 a=+20.21 b=+52.09. Overcolor is orange-red (L=42.25; a=+35.93; b=29.82). The red blush over the surface of the fruit varies with extent of direct exposure to sun light and may vary from 0 to 40 percent with an average of about 20 percent.

Pubescence: Very slight.

Suture: Very shallow extending from base to apex; slightly more pronounced at stem end.

Base: Retuse.

Apex: Rounded to slightly depressed, pistil point slightly depressed.

Cavity: Elongated; average width 1.24 cm (0.5 inches at right angle to suture plane; average width 2.04 (0.80 inches) in suture plane; average length 2.53 cm (1 inch).

Maturity: Ripens approximately 1 week prior to the cultivar "Harcot" when grown at Cream Ridge, N.J., usually according to data at Cream Ridge from June 9 to as late as July 3. Fruit ripens uniformly on the tree, developing ripe color about one week before dropping.

Use: Early maturing, excellent quality, dessert and canning apricot.

FLESH

Thickness: Medium.

Color: Tangerine orange Plant 24a to 24b.

Texture: Fine nearly non-melting.

Firmness: Very firm, moderately juicy.

Eating quality: Excellent; very sweet and aromatic.

Flavor: Fruit is moderately acidic, balanced by sweetness. Sweeter than most apricot cultivars, with strong apricot flavor and aroma. Quite juicy.

Quality: Maintained in cold storage for about three weeks and cannot be stored on the tree.

STONE

Type: Freestone.
Shape: Ovid.
Size: Small to medium. Average length 2.5 cm (1.0 inches); average width 1.9 cm (0.75 inches).
Ridges: Slight ridges extending along both sides of the suture plane.
Tendency to split: None.
Surface: Irregular, slightly pitted.
Color: Cinnamon Plate 16c (L=52.72; a=+10.11; b=+27.65).

TREE

Size: Medium.
Bark color (2 inch diameter limb): 178c to 178b.
Bark texture (2 inch diameter limb): Moderately smooth with prominent lenticels.
Vigor: Moderately vigorous.
Growth: Upright.
Production: Productive, but susceptible to spring frost damage.
Bearer: Regular.

LEAVES

Average size: Length 7.8 cm (3.1 inches); width 7.4 cm (2.9 inches).
Form: Ovate, abruptly acuminate, obtuse at base.
Thickness: Medium.

Margin: Serrate.
Color: Adaxial surface green Plat 137a to 137b (L=38.41; a=−13.43; b=+18.31); abaxial surface yellow-green Plate 147c to 147b (L=47.43; a=−13.13; b=+19.92).

FLOWERS

Mature:

*Flower width.*—Variable: 0.79–0.89 inches.
*Petal width.*—0.34 inches.
*Petal length.*—0.45 inches.
*Anther number.*—Variable; typically 25, 30, or even 35.
*Anther length.*—Variable; 0.24–0.38 inches.
*Pistil length.*—Variable; 0.34–0.41 inches.
*Petiole.*—Average length 3.5 cm (1.4 inches); average thickness 0.16 cm (0.0625 inches).
*Glands.*—Form globose; average number 3.7; variable in number primarily found on petiole.

I claim:

1. A new and distinct apricot tree cultivar, substantially as herein shown and described, characterized particularly as to novelty by the moderately vigorous, upright growth habit of the tree, on peach rootstock, excellent dessert and canning quality of the fruit which matures early, and is globose, slightly compressed in shape.

* * * * *